(12) United States Patent
Horcajada et al.

(10) Patent No.: US 11,504,387 B2
(45) Date of Patent: Nov. 22, 2022

(54) BIOCONVERSION OF OLEUROPEIN

(71) Applicant: SOCIETE DES PRODUITS NESTLE S.A., Vevey (CH)

(72) Inventors: Marie Noelle Horcajada, Echenevex (FR); Stephane Duboux, St-Prex (CH); Laure Poquet, Servion (CH)

(73) Assignee: Societe des Produits Nestle S.A., Vevey (CH)

( * ) Notice: Subject to any disclaimer, the term of this patent is extended or adjusted under 35 U.S.C. 154(b) by 84 days.

(21) Appl. No.: 16/762,400

(22) PCT Filed: Nov. 8, 2018

(86) PCT No.: PCT/EP2018/080543
§ 371 (c)(1),
(2) Date: May 7, 2020

(87) PCT Pub. No.: WO2019/092065
PCT Pub. Date: May 16, 2019

(65) Prior Publication Data
US 2020/0261487 A1 Aug. 20, 2020

(30) Foreign Application Priority Data
Nov. 8, 2017 (EP) .................................. 17200582

(51) Int. Cl.
| | | |
|---|---|---|
| *A61K 39/00* | (2006.01) | |
| *A61K 45/00* | (2006.01) | |
| *A01N 59/16* | (2006.01) | |
| *A61K 33/32* | (2006.01) | |
| *A61K 39/09* | (2006.01) | |
| *A61K 39/085* | (2006.01) | |
| *A01N 63/00* | (2020.01) | |
| *A61K 35/741* | (2015.01) | |
| *A61K 35/745* | (2015.01) | |
| *A61K 35/747* | (2015.01) | |
| *A61K 31/7048* | (2006.01) | |
| *A61K 9/00* | (2006.01) | |
| *A61K 38/46* | (2006.01) | |
| *A61K 38/47* | (2006.01) | |
| *A61K 35/00* | (2006.01) | |

(52) U.S. Cl.
CPC ........ *A61K 31/7048* (2013.01); *A61K 9/0053* (2013.01); *A61K 35/741* (2013.01); *A61K 38/465* (2013.01); *A61K 38/47* (2013.01); *A61K 2035/115* (2013.01)

(58) Field of Classification Search
CPC .................................................. A61K 31/7048
See application file for complete search history.

(56) References Cited

U.S. PATENT DOCUMENTS

| | | | |
|---|---|---|---|
| 9,132,145 B2 | 9/2015 | Lee-Huang et al. | |
| 2008/0014322 A1 | 1/2008 | Ibarra et al. | |
| 2014/0105875 A1* | 4/2014 | Bolster ................ | A61K 35/747 424/93.4 |
| 2014/0248247 A1* | 9/2014 | Bergonzelli Degonda .................... | A23L 33/135 424/93.45 |
| 2016/0045519 A1* | 2/2016 | Horcajada ............ | A61K 31/351 514/27 |
| 2016/0101125 A1* | 4/2016 | Horcajada .............. | A61K 36/74 424/94.1 |
| 2016/0120891 A1* | 5/2016 | Horcajada ............... | A61P 19/02 424/94.65 |
| 2016/0263139 A1* | 9/2016 | Horcajada .......... | A61K 31/7028 |
| 2019/0364949 A1* | 12/2019 | Bedard ..................... | A61P 3/04 |
| 2020/0170988 A1* | 6/2020 | Rodriguez Vilaboa ...................... | A61K 31/047 |
| 2020/0360409 A1* | 11/2020 | Horcajada ............ | A61K 35/745 |

FOREIGN PATENT DOCUMENTS

WO   WO 2014/161872 A1 * 10/2014

OTHER PUBLICATIONS

Naseeb et al., Nutrition Research, 2017; 40:1-20 (Year: 2017).*

(Continued)

*Primary Examiner* — Gary B Nickol
*Assistant Examiner* — Lakia J Jackson-Tongue
(74) *Attorney, Agent, or Firm* — K&L Gates LLP

(57) ABSTRACT

A composition contains at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. The at least one probiotic can form one or more of oleuropein aglycone, elenolic acid, hydroxytyrosol acetate or hydroxytyrosol from oleuropein. The composition can comprise oleuropein. The composition can be for treating or preventing impaired mobility in an older adult; stimulating bone formation and/or inhibiting bone resorption; treating or preventing synovitis in an individual in need or at risk thereof or treating or preventing articular cartilage degradation subsequent to synovitis in an individual having or recovering from synovitis; or preventing or treating cartilage breakdown.

10 Claims, 2 Drawing Sheets

(56) References Cited

OTHER PUBLICATIONS

Denison et al., Clinical Interventions in Aging, 2015; 10:859-869 (Year: 2015).*
Mahoney, Clin Geriatr Med. Nov. 1998; 14(4):699-726 (Year: 1998).*
Fairhall et al., BMC Med., 2011; 9:83 (Year: 2011).*
Cleveland Clinic, https://my.clevelandclinic.org/health/diseases/4443-osteoporosis; accessed on Sep. 17, 2021 (Year: 2021).*
Centers for Disease Control and Prevention, https://www.cdc.gov/arthritis/basics/osteoarthritis.htm; accessed on Sep. 17, 2021 (Year: 2021).*
The Orthopedic clinic, https://orthotoc.com/synovitis/, Jan. 4, 2019 (Year: 2019).*
Sokoll et al., Expert Opin. Pharmacother. (2006) 7(1):35-46 (Year: 2006).*
Core, blog: symptoms, causes and effective management of knee cartilage damage; Sep. 23, 2016; https://www.ossurwebshop.co.uk/blog/symptoms-causes-and-effective-management-of-cartilage-damage (Year: 2016).*
Varela-Eirin et al. "Olive-derived oleuropein as a potential treatment for bone and cartilage age-related disorders" Osteoarthritis and Cartilage, 2016, vol. 24, XP029467430.
Kok-Yong Chin et al. "Olives and Bone: A Green Osteoporosis Prevention Option" International Journal of Environmental Research and Public Health, Jul. 26, 2016, vol. 13, No. 8, p. 755, XP055539291.
Santos et al. "Bioconversion of oleuropein to hydroxytyrosol by lactic acid bacteria" World Journal of Microbiology and Biotechnology, Mar. 20, 2012, vol. 28, No. 6, pp. 2435-2440, XP035053735.

* cited by examiner

BIOCONVERSION OF OLEUROPEIN

CROSS REFERENCE TO RELATED APPLICATIONS

The present application is a National Stage of International Application No. PCT/EP2018/080543, filed on Nov. 8, 2018, which claims priority to European Patent Application No. 17200582.9, filed on Nov. 8, 2017, the entire contents of which are being incorporated herein by reference.

BACKGROUND

The present disclosure generally relates to compositions for the maintenance or improvement of bone and/or cartilage health. The compositions can additionally or alternatively prevent, alleviate and/or treat bone and/or cartilage disorders. More specifically, the present disclosure relates to co-administration of oleuropein and a probiotic that performs bioconversion of the oleuropein.

Bone mass evolves throughout life and is regulated by genetic, mechanical and hormonal mechanisms. Bone mineral acquisition occurs during childhood, and peak bone mass is achieved around twenty years of age. During this period, bone formation exceeds bone resorption. Later in life, and particularly around the time of the menopause or in the elderly population, bone mass and quality are impaired due to a higher bone turnover, with excessive bone resorption leading to a gradual loss of bone mass, microarchitecture, structure and strength.

Restoration of the balance between bone formation and bone resorption is important in order to maintain bone. This bone remodelling process is regulated at the cell level of the bone, involving a tight interaction between bone-forming cells (osteoblasts) and bone-resorbing cells (osteoclasts). In a healthy adult (man or animal), the coordinated action of the osteoblasts and osteoclasts maintains bone mass over time and simultaneously ensures remodelling of bone tissue by resorption and de novo synthesis of bone.

In a healthy adult, the rate of formation of the osteoclasts and osteoblasts achieves a balance between bone formation and bone resorption. However, in osteoporotic individuals, an imbalance in the process of bone remodelling is produced which culminates in a loss of bone proceeding more rapidly than the rate of formation. This imbalance exists to some extent in most individuals as they age but is much more severe and occurs at a younger age in osteoporotic individuals. Thus, in man and other mammals, a great variety of disorders is related to abnormal metabolism of bone resorption and bone formation, leading to an imbalance in metabolism or bone remodelling.

Moreover, in man and animals, there are many conditions characterized by the need to increase bone formation. For example, bone fractures necessitate stimulated bone growth in order to accelerate complete repair of the bone. This need is also present in the periodontal diseases, the metastatic diseases of bone, the osteolytic diseases and the conditions under which repair of the connective tissue is required, for example for the cicatrisation or regeneration of defects or traumatisms of cartilage. The stimulation of bone growth is also required in the case of primary and secondary hyperparathyroidism, as well as in osteoporosis associated with diabetes and in osteoporosis associated with glucocorticoids.

The current treatments for stimulating bone formation and/or inhibiting bone resorption have limited success.

Another joint disorder is osteoarthritis, which is a first cause of disability in the elderly. Osteoarthritis is a degenerative disease of the articular cartilage of the joint and is the most common form of arthritis, affecting 10% of the adult population. The main features of osteoarthritis are progressive breakdown and loss of the articular cartilage, accompanied by changes to other joint structures such as synovial membrane proliferation, sclerosis and thickness of subchondral bone, osteophyte formation at joint margin, ligament laxity and muscle atrophy, all of which contribute to the clinical symptoms of osteoarthritis. These symptoms include severe pain, stiffness, loss of joint motion and disability.

Currently, no cure exists for osteoarthritis, and therapy is only palliative, aiming at improving symptoms. For example, pain and inflammation are treated using analgesics (such as acetaminophen) and non-steroidal anti-inflammatory drugs (NSAIDs). Furthermore, the use of these drugs is often associated with side effects such as gastrointestinal or cardiovascular risks.

SUMMARY

Oleuropein is a polyphenol found in the fruit, the roots, the trunk and more particularly in the leaves of plants belonging to the Oleaceae family, and especially *Olea europaea*. The present inventors noted that in vitro data generated on chondrocytes metabolism obtained significant positive results with the oleuropein metabolite hydroxytyrosol, which showed higher efficacy compared to oleuropein. Without being bound by theory, based on the literature the present inventors believe that the chemical structure of hydroxytyrosol suggests that hydroxytyrosol has a higher bioavailability than oleuropein. Again without being bound by theory, the present inventors further believe that a portion of a dose of oleuropein can be absorbed as such in the intestinal upper level and another portion can reach the colon where it would mainly be absorbed after bioconversion into hydroxytyrosol and/or an intermediate metabolite such as oleuropein aglycone or hydroxytyrosol acetate.

Enhanced absorption of a metabolite of oleuropein at the colon could increase bioavailability of the oleuropein and thereby potentially increase the efficacy of the oleuropein. In this regard, co-administration of oleuropein with one or more probiotics having a glycosidase activity and/or an esterase activity can increase the presence of this probiotic in the colon to allow the degradation in situ of the oleuropein in order to optimize the absorption and consequent effect of a metabolite thereof.

Accordingly, in a general embodiment, the invention provides a composition for the treatment and prevention of a condition in an individual, the condition being selected from the group consisting of (i) loss of bone or cartilage metabolism balance, (ii) loss of bone or cartilage health, (iii) loss of mobility, (iv) synovitis, and (v) combinations thereof, wherein the composition comprises a combination of oleuropein and at least one probiotic or enzyme selected from the group consisting of (i) a probiotic having β-glycosidase activity (for example β-glucosidase activity) or a β-glycosidase (for example a β-glucosidase), (ii) a probiotic having esterase activity or an esterase, (iii) a probiotic having both β-glycosidase activity and esterase activity (for example both β-glucosidase activity and esterase activity) or an enzyme having both β-glycosidase activity and esterase activity (for example both β-glucosidase activity and esterase activity), (iv) a first probiotic having β-glycosidase activity (for example β-glucosidase activity) and a second probiotic having esterase activity, (v) a probiotic having β-glycosidase activity (for example β-glucosidase activity) and an esterase, (vi) a β-glycosidase (for example a β-glucosidase) and a probiotic having esterase activity and (vii) a β-glycosidase (for example a β-glucosidase) and an esterase, the composition comprising an amount of the at least one probiotic or enzyme that is effective to achieve an effect. For example the composition may comprise a combination of oleuropein and at least one probiotic selected from the group consisting of (i) a probiotic having β-glycosidase activity (for example a β-glucosidase activity), (ii) a probiotic having esterase activity, (iii) a probiotic having both β-glycosidase activity (for example β-glucosidase activity) and esterase activity and (iv) a first probiotic having β-glycosidase activity (for example a β-glucosidase activity) and a second probiotic having esterase activity. For further example, the composition may be a composition to be co-administered with oleuropein, for example an effective amount of oleuropein.

For example, the invention may provide a composition for the treatment and prevention of a condition in an individual, the condition being selected from the group consisting of (i) loss of bone or cartilage metabolism balance, (ii) loss of bone or cartilage health, (iii) loss of mobility, (iv) synovitis, and (v) combinations thereof, wherein the composition comprises a combination of oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase, the composition comprising an amount of the combination that is effective to achieve an effect. For example the composition may comprise at least one probiotic selected from the group consisting of (i) a probiotic having β-glycosidase activity, (ii) a probiotic having esterase activity, (iii) a probiotic having both β-glycosidase activity and esterase activity and (iv) a first probiotic having β-glycosidase activity and a second probiotic having esterase activity.

In an embodiment, the invention provides a composition for the treatment and prevention of a condition in an individual wherein the individual is a low absorber or a non absorber of oleuropein. For example, the individual may have an intestinal microbiota lacking or low in bacteria having β-glycosidase activity and/or lacking or low in bacteria having esterase activity.

In an embodiment, the composition is for the treatment or prevention of loss of mobility, wherein the individual is an older adult having a condition selected from the group consisting of frailty, pre-frailty, sarcopenia, recovering from sarcopenia, osteoporosis, osteoarthritis, malnutrition, being at risk of malnutrition, undergoing rehabilitation, scheduled to undergo rehabilitation within the next year, and combinations thereof. For example, the older adult may be an elderly individual.

In an embodiment the composition is for the treatment or prevention of loss of bone metabolism balance wherein the individual has a condition selected from the group consisting of osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof.

In an embodiment, the composition is for the treatment of synovitis in an individual in need thereof, or articular cartilage degradation subsequent to synovitis in an individual having or recovering from synovitis, wherein the synovitis is associated with a condition selected from the group consisting of lupus, gout, rheumatoid arthritis, osteoarthritis, osteochondritis disease, osteoarthrosis and combinations thereof.

In an embodiment, the at least one probiotic in the composition of the invention forms an oleuropein metabolite selected from the group consisting of oleuropein aglycone, hydroxytyrosol acetate, hydroxytyrosol, elenolic acid and mixtures thereof. For example, the at least one probiotic in the composition of the invention may form an oleuropein metabolite selected from the group consisting of oleuropein aglycone, elenolic acid and mixtures thereof.

In another embodiment, the invention provides a composition for the potentiation of a therapeutic effect and/or a prophylactic effect of oleuropein in an individual, the composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase, the composition comprising an amount of the at least one probiotic or enzyme that is effective to achieve an effect to the individual. For example the composition for the potentiation of a therapeutic effect and/or a prophylactic effect of oleuropein in an individual may comprise at least one probiotic selected from the group consisting of (i) a probiotic having β-glycosidase activity, (ii) a probiotic having esterase activity, (iii) a probiotic having both β-glycosidase activity and esterase activity and (iv) a first probiotic having β-glycosidase activity and a second probiotic having esterase activity. The at least one probiotic of the composition of the invention may form an oleuropein metabolite selected from the group consisting of oleuropein aglycone, hydroxytyrosol acetate, hydroxytyrosol, elenolic acid and mixtures thereof. The oleuropein and the oleuropein metabolite may provide the therapeutic effect and/or the prophylactic effect for a longer duration than would be obtained by administration of the oleuropein metabolite by itself.

The dietary benefits of olive polyphenols are enjoyed by healthy individuals. Olives have strong consumer acceptance as a healthy food. Generating olive polyphenol metabolites in food and beverages is beneficial to healthy individuals, for example when the metabolites provide enhanced bio-availability and efficacy of the olive polyphenols. In a further embodiment, the invention provides for the non-therapeutic use of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase, the composition comprising an amount of the at least one probiotic or enzyme that is effective to achieve an effect. For example the invention may provide the non-therapeutic use of a composition comprising at least one probiotic selected from the group consisting of (i) a probiotic having β-glycosidase activity, (ii) a probiotic having esterase activity, (iii) a probiotic having both β-glycosidase activity and esterase activity and (iv) a first probiotic having β-glycosidase activity and a second probiotic having esterase activity.

In an embodiment, the composition is to be co-administered with oleuropein, for example an effective amount of oleuropein.

In an embodiment, the composition comprises oleuropein, for example in an effective amount.

In an embodiment, the probiotic having β-glycosidase activity has β-glucosidase activity.

In an embodiment, the β-glycosidase enzyme is an β-glucosidase.

In an embodiment, the composition of the invention is for oral administration. The composition may additionally comprise an excipient or a pharmaceutically acceptable carrier.

In an embodiment, the at least enzyme in the composition of the invention comprises a β-glucosidase. For example the at least one enzyme may be selected from the group consisting of an enzyme without esterase activity, an enzyme with esterase activity, and a mixture thereof.

In an embodiment, the at least one probiotic in the composition of the invention comprises a probiotic having β-glucosidase activity. For example the at least one probiotic having β-glycosidase activity may be selected from the group consisting of a probiotic without esterase activity, a probiotic with esterase activity, and a mixture thereof.

In an embodiment, the composition of the invention is a food or beverage product.

In an embodiment, the composition is a nutritional supplement.

In an embodiment, the composition of the invention further comprises a component selected from the group consisting of protein, carbohydrate, fat and combinations thereof.

In an embodiment, the composition of the invention further comprises a food additive selected from the group consisting of acidulants, thickeners, buffers or agents for pH adjustment, chelating agents, colorants, emulsifiers, flavor agents, minerals, osmotic agents, preservatives, stabilizers, sugars, sweeteners, texturizers, vitamins, minerals and combinations thereof.

The present disclosure provides a method of treating or preventing impaired mobility in an older adult. The method comprises orally administering to the older adult an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For example the method may comprise orally administering to the older adult an effective amount of a composition comprising oleuropein at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For example, the method may comprise orally administering to the older adult an effective amount of a composition comprising at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity. For example the method may comprise orally administering to the older adult an effective amount of a composition comprising oleuropein and at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity.

In an embodiment, the older adult is an elderly individual.

In an embodiment, the older adult has a condition selected from the group consisting of frailty, pre-frailty, sarcopenia, recovering from sarcopenia, osteoporosis, osteoarthritis, malnutrition, at risk of malnutrition, undergoing rehabilitation, scheduled to undergo rehabilitation within the next year, and combinations thereof.

In an embodiment, the composition is administered daily for at least one month.

In an embodiment, the at least one probiotic forms an oleuropein metabolite selected from the group consisting of oleuropein aglycone, hydroxytyrosol acetate, hydroxytyrosol, elenolic acid and mixtures thereof.

In another embodiment, the present disclosure provides a method for stimulating bone formation and/or inhibiting bone resorption in an individual having a condition comprising an imbalance between bone formation and bone resorption. The method comprises orally administering to the individual an effective amount of a composition comprising at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For example the method may comprise orally administering to the individual an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For example, the method may comprise orally administering to the individual an effective amount of a composition comprising at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity. For example the method may comprise orally administering to the individual an effective amount of a composition comprising oleuropein and at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity.

In an embodiment, the condition is selected from the group consisting of osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof.

In another embodiment, the present disclosure provides a method of treating synovitis in an individual in need thereof, preventing synovitis in an individual at risk thereof, or treating or preventing articular cartilage degradation subsequent to synovitis in an individual having or recovering from synovitis. The method comprises orally administering to the individual an effective amount of a composition comprising at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For example the method may comprise orally administering to the individual an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For further example the method may comprise orally administering to the individual an effective amount of a composition comprising at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity. For example the method may comprise orally administering to the individual an effective amount of a composition comprising oleuropein and at least one probiotic selected from the group consisting of (i) a probiotic having β-glycosidase activity, (ii) a probiotic having esterase activity, (iii) a probiotic having both β-glycosidase activity and esterase activity and (iv) a first probiotic having β-glycosidase activity and a second probiotic having esterase activity.

In an embodiment, the synovitis is associated with a condition selected from the group consisting of lupus, gout, rheumatoid arthritis, osteoarthritis, osteochondritis disease, osteoarthrosis and combinations thereof.

In another embodiment, the present disclosure provides a method of preventing or treating cartilage breakdown in an individual. The method comprises orally administering to the individual an effective amount of a composition comprising at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. For example, the method may comprise orally administering to the individual an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity or an enzyme having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase. The method may comprise orally administering to the individual an effective amount of a composition comprising at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity. For example, the method may comprise orally administering to the individual an effective amount of a composition comprising oleuropein and at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity.

In another embodiment, the present disclosure provides a composition to be co-administered with oleuropein, the composition comprising at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity. The composition comprises an amount of the at least one probiotic that is effective to achieve an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof.

In another embodiment, the present disclosure provides a composition comprising a combination of oleuropein and at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity. The composition comprises an amount of the combination that is effective to achieve an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof.

In another embodiment, the present disclosure provides a method of making a composition for achieving an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof. The method comprises adding an effective amount of a combination of oleuropein and at least one probiotic selected from the group consisting of (i) a probiotic having β-glycosidase activity (preferably β-glucosidase activity), (ii) a probiotic having esterase activity, (iii) a probiotic having both β-glycosidase activity and esterase activity and (iv) a first probiotic having β-glycosidase activity and a second probiotic having esterase activity, to at least one ingredient selected from the group consisting of protein, carbohydrate, and fat.

In another embodiment, the present disclosure provides a method of making a composition for achieving an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof wherein the composition is to be co-administered with oleuropein. The method comprises adding an effective amount of at least one probiotic selected from the group consisting of (i) a probiotic having β-glucosidase activity (preferably β-glucosidase activity), (ii) a probiotic having esterase activity, (iii) a probiotic having both β-glycosidase activity and esterase activity and (iv) a first probiotic having β-glucosidase activity and a second probiotic having esterase activity, to at least one ingredient selected from the group consisting of protein, carbohydrate, and fat.

In an embodiment, the method further comprises adding to the at least one ingredient a food additive selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

In another embodiment, the present disclosure provides a method of potentiating a therapeutic effect and/or a prophylactic effect of oleuropein in an individual. The method comprising orally administering at least one probiotic selected from the group consisting of (i) a probiotic having β-glucosidase activity (preferably β-glucosidase activity), (ii) a probiotic having esterase activity, (iii) a probiotic having both β-glucosidase activity and esterase activity and (iv) a first probiotic having β-glucosidase activity and a second probiotic having esterase activity to the individual. The at least one probiotic may be administered to the individual in the same composition as the oleuropein such that the at least one probiotic and the oleuropein are administered concurrently. The at least one probiotic may be administered to the individual in a composition separate from the oleuropein.

Preferably, the at least one probiotic forms an oleuropein metabolite selected from the group consisting of oleuropein aglycone, hydroxytyrosol acetate, hydroxytyrosol, elenolic acid and mixtures thereof; and the oleuropein and the oleuropein metabolite provide the therapeutic effect and/or the prophylactic effect for a longer duration than would be obtained by administration of the oleuropein metabolite by itself.

An advantage of one or more embodiments provided by the present disclosure is mobility in aging, frail or pre-frail individuals, for example such individuals who are recovering from rehabilitation or at risk of sarcopenia, and particularly bone and joint benefits in such individuals.

Another advantage of one or more embodiments provided by the present disclosure is to treat or prevent osteopenia (mild loss of bone mass), promote bone growth in young individuals, and/or treat or prevent disorders linked with an unbalanced ratio between bone formation and bone resorption.

Yet another advantage of one or more embodiments provided by the present disclosure is to stimulate bone formation or inhibit bone resorption in a subject suffering from osteoporosis, osteolysis adjacent a prosthesis, periodontal disease, osteoarthritis and/or osteopenia.

Still another advantage of one or more embodiments provided by the present disclosure is to enhance bone formation and/or cartilage anabolism; prevent or treat cartilage breakdown; and/or limit synovitis and the subsequent articular cartilage degradation (osteoarthritis) during aging.

An additional advantage of one or more embodiments provided by the present disclosure is to increase the potential efficacy of oleuropein following oral intake thereof, by increasing its bioavailability through enhancing its absorption at the colon and thus providing efficacy from at least two sites of absorption and at least two circulating compounds, namely the parent compound and one or more metabolites (e.g., dual efficacy). This leads to a greater protective effect.

Another advantage of one or more embodiments provided by the present disclosure is to perform bioconversion on the portion of oleuropein that reaches the colon after the partial absorption of oleuropein in the small intestine; higher absorption of 3,4-dihydroxyphenolethanol-elenolic acid (also known as oleuropein aglycone and 3,4-DHPEA-EA) and/or hydroxytyrosol and/or hydroxytyrosol acetate and/or elenolic acid is expected in the colon.

Yet another advantage of one or more embodiments provided by the present disclosure is to providing a longer duration of the therapeutic effect of a dose of oleuropein, possibly by providing an extended absorption over time in which the oleuropein or a metabolite thereof is absorbed at two different levels: small intestine, and colon. With the metabolites being generated faster due to co-administration of oleuropein and probiotics or enzymes, the onset of their bioavailability may be sooner, leading to a longer overall period of absorption.

Still another advantage of one or more embodiments provided by the present disclosure is to boost the microflora of an elderly individual.

An additional advantage of one or more embodiments provided by the present disclosure is to decrease the dose of oleuropein intake while achieving the same efficacy.

Additional features and advantages are described herein and will be apparent from the following Figures and Detailed Description.

DETAILED DESCRIPTION

Definitions

Figure 1:
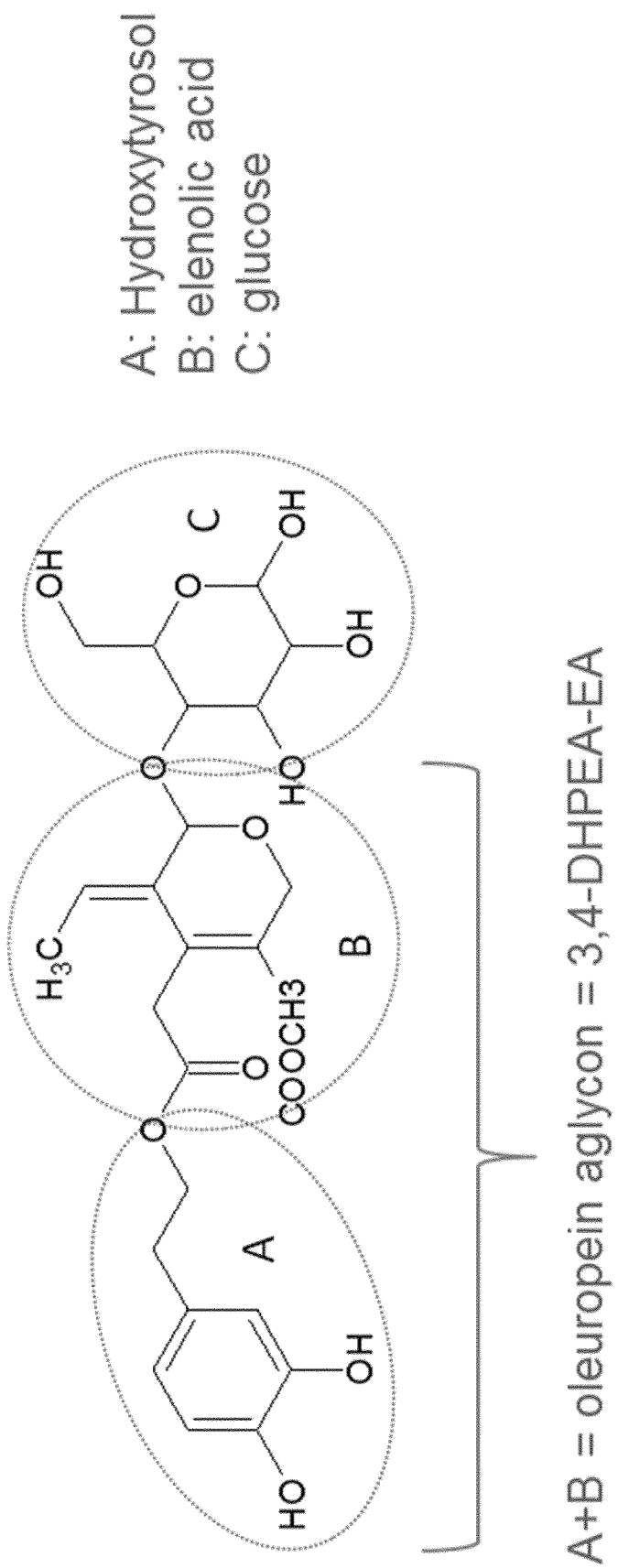
FIG. 1 shows the chemical structure of oleuropein.

Some definitions are provided hereafter. Nevertheless, definitions may be located in the "Embodiments" section below, and the above header "Definitions" does not mean that such disclosures in the "Embodiments" section are not definitions.

Probiotics are micro-organisms that when administered in adequate amounts confer health benefits to the host.

All percentages expressed herein are by weight of the total weight of the composition unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. As used herein, "associated with" and "linked with" mean occurring concurrently, preferably means caused by the same underlying condition, and most preferably means that one of the identified conditions is caused by the other identified condition.

In the context of the present invention, the term individuals is not limited to humans. Individuals may for example be humans, livestock or companion animals.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the elements disclosed herein, as well as any additional or optional ingredients, components, or elements described herein or otherwise useful in a diet.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly individuals.

"Sarcopenia" is defined as the age-associated loss of muscle mass and functionality (including muscle strength and gait speed).

As used herein, "frailty" is defined as a clinically recognizable state of increased vulnerability resulting from aging-associated decline in reserve and function across multiple physiologic systems such that the ability to cope with everyday or acute stressors is compromised. In the absence of an established quantitative standard, frailty has been operationally defined by Fried et al. as meeting three out of five phenotypic criteria indicating compromised energetics: (1) weakness (grip strength in the lowest 20% of population at baseline, adjusted for gender and body mass index), (2) poor endurance and energy (self-reported exhaustion associated with VO2 max), (3) slowness (lowest 20% of population at baseline, based on time to walk 15 feet, adjusting for gender and standing height), (4) low physical activity (weighted score of kilocalories expended per week at baseline, lowest quintile of physical activity identified for each gender; e.g., less than 383 kcal/week for males and less than 270 kcal/week for females), and/or unintentional weight loss (10 lbs. in past year). Fried L P, Tangen C M, Walston J, et al., "Frailty in older adults: evidence for a phenotype." J. Gerontol. A. Biol. Sci. Med. Sci. 56(3):M146M156 (2001).

A pre-frail stage, in which one or two of these criteria are present, identifies a high risk of progressing to frailty.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition disclosed herein, namely a composition comprising oleuropein and a probiotic capable of bioconversion of the oleuropein, relative to a composition lacking the probiotic but otherwise identical.

Embodiments

FIG. 1 shows the chemical structure of oleuropein. Oleuropein is a heterosidic ester of 3,4-dihydroxyphenylethanol (also known as hydroxytyrosol, labeled as "A" in FIG. 1) and elenolic acid (labeled as "B" in FIG. 1) containing a molecule of glucose (labeled as "C" in FIG. 1). The mechanism of oleuropein absorption is not clear. Nevertheless, oleuropein resists degradation in the upper gastrointestinal tract and the small intestine, and thus at least a portion of a dose of oleuropein will reach the colon. Microflora in the colon can then perform bioconversion on this oleuropein.

Figure 2:
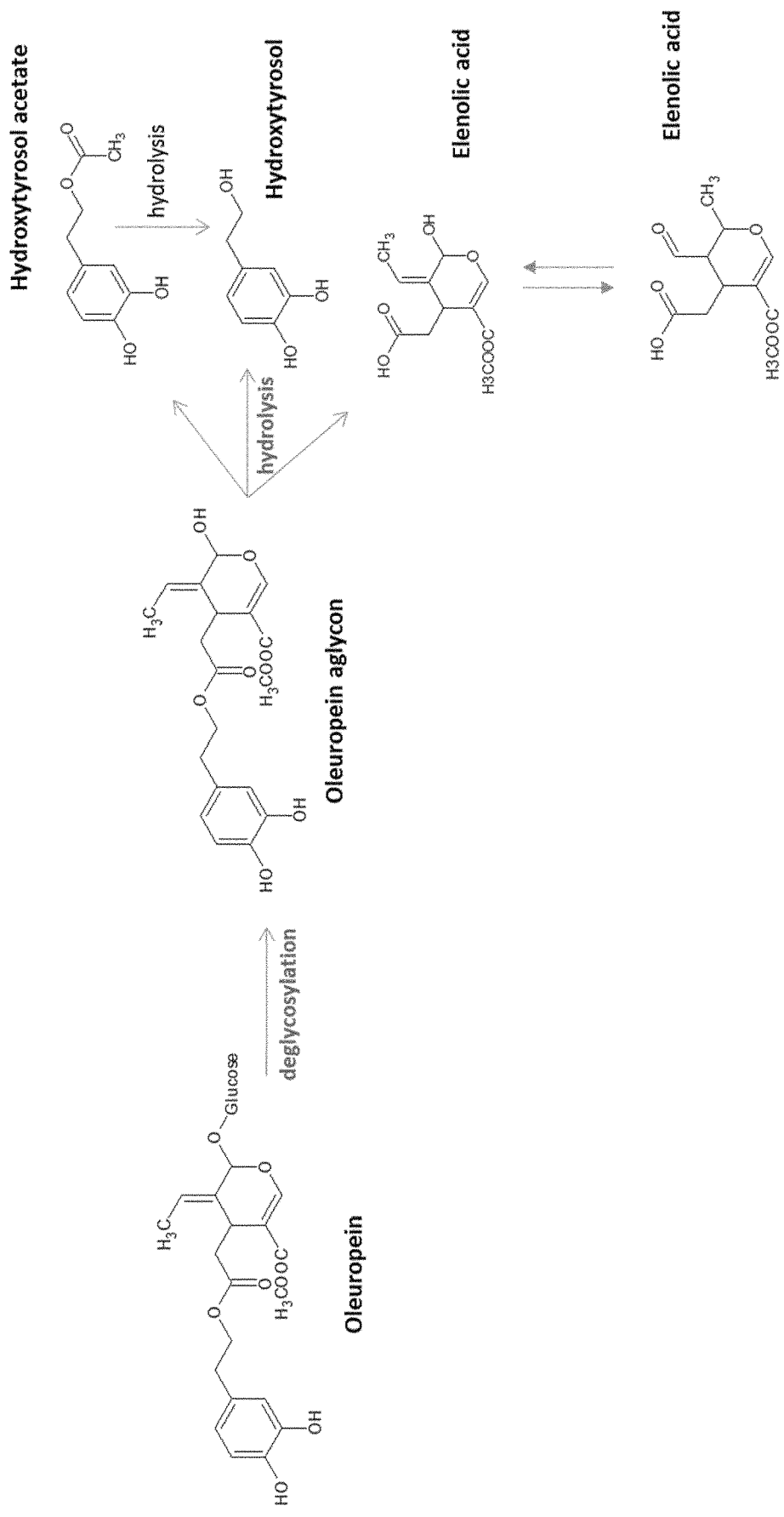
FIG. 2 shows the bioconversion of oleuropein by microflora.

As shown in FIG. 2, deglycosylation converts the oleuropein to oleuropein aglycone (also known as 3,4-dihydroxyphenylethanol-elenolic acid or "3,4-DHPEA-EA"). Then hydrolysis (e.g., by an esterase) can form hydroxytyrosol acetate and/or elenolic acid, and further hydrolysis can form hydroxytyrosol from the hydroxytyrosol acetate.

According to the literature, oleuropein aglycone is 2.2 times less absorbed compared with hydroxytyrosol, but 13.5 times more absorbed than oleuropein. Oleuropein aglycone has a slower clearance from the plasma compared with hydroxytyrosol and oleuropein. Moreover, oleuropein aglycone has an antioxidant activity comparable to that of caffeic acid, oleuropein and hydroxytyrosol.

Hydroxytyrosol absorption is higher than oleuropein and oleuropein aglycone, and hydroxytyrosol acetate absorption is even higher than that of hydroxytyrosol. In this regard, hydroxytyrosol acetate is more soluble in the lipophilic phases than hydroxytyrosol due to the presence of the ester group in hydroxytyrosol acetate. The present inventors believe that this increased lipophilicity suggests that hydroxytyrosol acetate is better absorbed across intestinal epithelial cell monolayers than free hydroxytyrosol.

Oleuropein can be absorbed as such in the upper gastrointestinal tract or can reach the colon were it would mainly be absorbed after bioconversion into oleuropein aglycone, hydroxytyrosol acetate, and/or hydroxytyrosol. However, the proportion of oleuropein not absorbed in the upper gastrointestinal tract and thus reaching the colon for further metabolism after bioconversion is not well defined. Therefore, without being bound by theory, the present inventors believe that enhancing absorption of oleuropein or a derivative thereof in the colon can increase the potential efficacy of the oleuropein following oral intake and thereby increase the bioavailability thereof. Indeed, enhanced absorption of oleuropein or a derivative thereof in the colon could provide efficacy from at least two sites of absorption and the at least two circulating compounds, namely the parent and one or more metabolites (e.g., dual efficacy).

Specifically, co-administration of oleuropein with one or more probiotics having β-glycosidase activity (preferably β-glucosidase activity) and/or esterase activity, can increase the presence of probiotics in the colon and thus allow the degradation in situ of oleuropein in order to optimize the absorption and consequent effect of oleuropein. For example, a probiotic having β-glycosidase activity, preferably β-glucosidase activity (and preferably not esterase activity) can convert the oleuropein into oleuropein aglycone in the colon. A probiotic having β-glycosidase activity (preferably β-glucosidase activity) and esterase activity can convert the oleuropein into hydroxytyrosol acetate and/or hydroxytyrosol and/or elenolic acid in the colon. Establishing and/or increasing the presence of such microorganisms in the colon can potentiate the effect of oleuropein administration, thereby providing an extended absorption over time with oleuropein (e.g., absorption at two different levels: small intestine, colon), for example absorption that is extended relative to hydroxytyrosol by itself which provides a more acute peak of absorption.

Accordingly, an aspect of the present disclosure is a method of maintaining or restoring bone metabolism balance by stimulating bone formation and/or preventing bone resorption. Another aspect of the present disclosure is a method of treating or preventing a disorder linked to cartilage turnover by stimulating cartilage anabolism through inhibiting or decreasing cartilage breakdown. Yet another aspect of the present disclosure is a method of preventing or treating a bone disorder (e.g., a disorder associated with an unbalanced bone formation: bone resorption ratio, such as osteoporosis) or for maintaining bone health. Other aspects of the present disclosure include a method of stimulating bone formation and/or cartilage anabolism during a growth period of a young individual, stimulating bone formation and/or cartilage anabolism in adults in order to increase maximal bone mass (e.g., in perimenopausal women, healthy adults, healthy aging adults, and adults who are pre-osteoarthritic), a method of treating or preventing bone loss which occurs with aging (osteopenia), a method of treating a bone deficiency resulting from a fracture, and a method of treating or preventing synovitis (e.g., synovitis associated with lupus, gout, or arthritis such as one or more of rheumatoid arthritis, osteoarthritis, osteochondritis disease, and osteoarthrosis).

In some embodiments, the composition is administered to treat or prevent impaired mobility in an older adult, for example by maintaining or improving joint functionality (e.g., bone functionality and/or cartilage functionality). The older adult can have a condition selected from the group consisting of frailty, pre-frailty, sarcopenia, recovering from sarcopenia, osteoporosis, osteoarthritis, malnutrition, at risk of malnutrition, undergoing rehabilitation, scheduled to undergo rehabilitation (e.g., within the next year, preferably within the next six months, more preferably within the next month), and combinations thereof.

The methods comprise orally administering an effective amount of a composition comprising oleuropein and at least one probiotic selected from the group consisting of (i) a probiotic having a β-glucosidase activity (preferably β-glucosidase activity) with esterase activity or without esterase activity, (ii) a probiotic having esterase activity with β-glycosidase activity or without β-glycosidase activity, (iii) a probiotic having both β-glycosidase activity and esterase activity and (iv) a first probiotic having β-glycosidase activity with esterase activity or without esterase activity and a second probiotic having esterase activity with β-glycosidase activity or without β-glucosidase activity to an individual, preferably a human. Optionally the composition can contain additional probiotics that do not have β-glucosidase activity or esterase activity.

The individual can be at risk of the disorder or condition, in which case the effective amount of the composition is a prophylactically effective dose; or the individual can have the disorder or condition, in which case the effective amount of the composition is a therapeutically effective dose. In some embodiments, the methods comprise identifying the individual as having the condition or being at risk of the condition before the administration.

For example, the at least one probiotic may belong to the *Lactobacillus, Bifidobacteria, Lactococcus* or *Streptococcus* genus, for example *Lactobacillus gasseri, Lactobacillus acidophilus, Lactobacillus salivarius, Lactobacillus rhamnosus, Lactobacillus paracasei* (for example *L. paracasei* LMG 9192), *Lactobacillus casei, Lactobacillus johnsonii, Lactobacillus plantarum* (for example *L. plantarum* LMG 6907), *Lactobacillus fermentum, Lactobacillus lactis, Lactobacillus delbrueckii, Lactobacillus helveticus, Lactobacillus brevis, Lactococcus lactis, Streptococcus salivarius, Streptococcus thermophilus, Bifidobacterium lactis, Bifidobacterium animalis, Bifidobacterium longum, Bifidobacterium breve, Bifidobacterium infantis, Bifidobacterium adolescentis, Bifidobacterium pseudocatenulatum* or mixtures thereof. For further example the probiotic may be selected from the group consisting of *Lactobacillus gasseri, Lactobacillus acidophilus, Lactobacillus salivarius, Lactobacillus rhamnosus, Lactobacillus johnsonii, Lactobacillus fermentum, Lactobacillus lactis, Lactobacillus delbrueckii, Lactobacillus helveticus, Lactobacillus brevis, Lactococcus lactis, Streptococcus salivarius, Streptococcus thermophilus, Bifidobacterium lactis, Bifidobacterium animalis, Bifidobacterium longum, Bifidobacterium breve, Bifidobacterium infantis, Bifidobacterium adolescentis, Bifidobacterium pseudocatenulatum* or mixtures thereof. Non-limiting examples of suitable strains include *B. longum* ATCC BAA-999, *B. longum* CNCM I-2618, *B. animalis* CNCM I-3446, *S. thermophilus* CNCM I-3915, *Lactobacillus paracasei* CNCM I-2116, *Lactobacillus rhamnosus* CGMCC 1.3724, *Lactobacillus johnsonii* CNCM I-1225 and *Lactococcus lactis* CNCM I-4154.

*B. longum* ATCC BAA-999 is publically available from ATCC.

*B. longum* CNCM I-2618, also named NCC 2705, was deposited with the Collection Nationale de Cultures de Microorganismes (CNCM), Institut Pasteur, 25 rue du Docteur Roux, F-75724 PARIS Cedex 15, France, on 29 Jan. 2001 and given the deposit number I-2618.

*B. animalis* CNCM I-3446, also named NCC 2818, was deposited with the Collection Nationale de Cultures de Microorganismes (CNCM), Institut Pasteur, 25 rue du Docteur Roux, F-75724 PARIS Cedex 15, France, on 7 Jun. 2005 and given the deposit number I-3446.

*S. thermophilus* CNCM I-3915, also named NCC 2496, was deposited with the Collection Nationale de Cultures de Microorganismes (CNCM), Institut Pasteur, 25 rue du Docteur Roux, F-75724 PARIS Cedex 15, France, on 5 Feb. 2008 and given the deposit number I-3915.

*Lactobacillus paracasei* CNCM I-2116, also named NCC 2461, was deposited with the Collection Nationale de Cultures de Microorganismes (CNCM), Institut Pasteur, 25 rue du Docteur Roux, F-75724 PARIS Cedex 15, France, on 12 Jan. 1999 and given the deposit number I-2116.

*Lactobacillus rhamnosus* CGMCC 1.3724, also named NCC 4007, was deposited at the China General Microbiological Culture Collection Centre, Beijing on October 2004 and given the deposit number 1,3724.

*Lactobacillus johnsonii* CNCM I-1225 also named La1, was deposited with the Collection Nationale de Cultures de Microorganismes (CNCM), Institut Pasteur, 25 rue du Docteur Roux, F-75724 PARIS Cedex 15, France, on 30 Jun. 1992 and given the deposit number I-1225.

*Lactococcus lactis* CNCM I-4154 also named NCC 2287, was deposited with the Collection Nationale de Cultures de Microorganismes (CNCM), Institut Pasteur, 25 rue du Docteur Roux, F-75724 PARIS Cedex 15, France, on 24 Apr. 2009 and given the deposit number I-4154.

The present disclosure is not limited to a specific embodiment of the at least one probiotic, and the probiotic can be any non-harmful microorganism having β-glycosidase activity and/or esterase activity. Such microorganisms can be identified by one or more of: identifying the probiotic strain using genomic in silico analysis on a plurality of strains, assessing the in vitro oleuropein bio conversion by the probiotic strain (microbial deglycosylation and/or hydrolysis), determining if the probiotic strain improves the bioavailability of oleuropein (optionally determining the effect of the carrier matrix), assessing in vitro efficacy using primary chondrocyte and osteoblast cultures, and/or using a clinical trial investigating the effect of oleuropein and the probiotic strain on bone and joint health outcomes.

The at least one probiotic forms an oleuropein metabolite selected from the group consisting of oleuropein aglycone, hydroxytyrosol acetate, hydroxytyrosol, elenolic acid and mixtures thereof. In some embodiments, the at least one probiotic comprises first and second probiotics that form different oleuropein metabolites relative to each other and/or different amounts of one or more of the oleuropein metabolites relative to each other.

In an embodiment, the composition is administered to the individual for a time period of at least one month; preferably at least two months, more preferably at least three, four, five or six months; most preferably for at least one year. During the time period, the composition can be administered to the individual at least one day per week; preferably at least two days per week, more preferably at least three, four, five or six days per week; most preferably seven days per week. The composition can be administered in a single dose per day or in multiple separate doses per day.

In an alternative embodiment, the oleuropein and the probiotic can be administered sequentially in separate compositions. The term "sequentially" means that the oleuropein and the probiotic are administered in a successive manner such that the oleuropein is administered at a first time without the probiotic, and the probiotic is administered at a second time subsequent to the first time without the oleuropein. The time between sequential administrations may be, for example, one or several seconds, minutes or hours in the same day; one or several days or weeks in the same month; or one or several months in the same year. The order of sequential administration may be reversed.

Further in this regard, "co-administration" of oleuropein and at least one probiotic or enzyme means that the at least one probiotic or enzyme is administered to an individual who has consumed oleuropein and/or will consume oleuropein and does not necessarily mean that they are administered at the same time in the same composition. Although concurrent administration is indeed preferred, the present disclosure is not limited to this embodiment. If the oleuropein and probiotic or enzyme are comprised within the same composition the oleuropein may be isolated from the probiotic or enzyme to prevent fermentation of the oleuropein on storage. For example, the probiotic or enzyme may be encapsulated separately from the oleuropein. Preferably the probiotic or enzyme only reacts with the oleuropein after administration, for example in the digestive tract of the individual.

In some embodiments, the composition is used in one of the methods disclosed by U.S. Patent App. Publ. Nos. 2016/0045519 and 2016/0120891 and International Patent App. Publ. No. WO 2015/055468, the entireties of which are incorporated herein by reference.

The effective amount of the composition varies with the particular composition, the age and condition of the recipient, and the particular disorder or disease being treated. Nevertheless, in a general embodiment, the composition can be administered to the individual in an amount that provides 0.01 mg to 2 g of the oleuropein per day, preferably from 0.1 mg to 1 g of the oleuropein per day, and more preferably from 1 mg to 200 mg of the oleuropein per day; and the composition can be administered to the individual in an amount that provides $10^5$ to $10^{12}$ colony forming units (cfu) of the probiotic per day, preferably from $10^7$ to $10^{11}$ cfu of the probiotic per day.

Some individuals can have bacterial flora containing probiotics that will already have β-glycosidase activity and/or esterase activity. Therefore, in some cases administration of the composition enhances the therapeutic and/or prophylactic effect of these probiotics by providing more of the bacteria.

Some individuals are unable to absorb oleuropein, or have a reduced ability to absorb oleuropein. For example, the individual may have an intestinal microbiota lacking or low in bacteria having β-glycosidase activity and/or lacking or low in bacteria having esterase activity. In such cases, administration of the composition enables the individual to enjoy the health benefits of olive polyphenols which would otherwise not have been possible, or would have been much reduced. The composition may be co-administered with oleuropein or provided as a separate composition to oleuropein.

In an embodiment, at least a portion of the oleuropein is obtained by extraction, e.g., by extraction from a plant such as a plant belonging to the Oleaceae family, preferably one or more of the stems, the leaves, the fruits or the stones of a plant belonging to the Oleaceae family such as *Olea europaea* (olive tree), a plant of genus *Ligustrum*, a plant of genus *Syringa*, a plant of genus *Fraximus*, a plant of genus *Jasminum* and a plant of genus *Osmanthus*. Additionally or alternatively, at least a portion of the oleuropein can be obtained by chemical synthesis.

Another aspect of the present disclosure is a method of making a composition for achieving an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof. The compositions and methods can additionally or alternatively prevent, alleviate and/or treat bone and/or cartilage disorders. The composition is preferably a food product.

The method comprises adding oleuropein and a probiotic capable of bioconversion of the oleuropein to an ingredient selected from the group consisting of a protein, a carbohydrate, a lipid, and combinations thereof. The composition (e.g., food product) can be made prior to administration (e.g., the composition is made, packaged, and then purchased by a consumer who administers the composition to themselves or to another individual) or can be made substantially simultaneous to administration (the composition is made less than 30 minutes before administration, preferably less than 15 minutes before administration, more preferably less than 10 minutes before administration, most preferably less than 5 minutes before administration, by an individual who administers the composition to themselves or to another individual).

The composition can comprise an effective amount of the combination of the oleuropein and the probiotic. For example, a single serving or dose of the composition can comprise the effective amount, and a package can contain one or more of the servings or doses.

The composition can comprise a food additive selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

The composition can comprise an additional ingredient for bone quality, for example protein, vitamin C, vitamin D, vitamin K2, calcium, phosphorus, magnesium, zinc, hesperidin (flavanone), or combinations thereof. The composition can comprise an additional for joint quality comprising at least one ingredient for short-term joint quality, for example, glucosamine (e.g., glucosamine sulfate), chondroitin (e.g., chondroitin sulfate), hyaluronic acid (e.g., a rooster comb extract rich in hyaluronic acid) or combinations thereof (preferably at least hyaluronic acid), and/or at least one ingredient for long-term joint quality, for example vitamin C, another polyphenol (e.g., curcumin, quercetin and/or rutin), omega-3 fatty acids, or combinations thereof. Non-limiting examples of other suitable additional ingredients for joint quality include collagen, hydrolyzed collagen, *Boswellia serrata*, rose hip, and combinations thereof.

The protein can be whey, e.g., native whey, intact unhydrolyzed whey, whey protein concentrate, whey protein isolate, acid whey, sweet whey, modified sweet whey (sweet whey from which the caseino-glycomacropeptide has been removed), a fraction of whey protein, or whey protein hydrolysate; casein; a vegetable protein such as soy protein; and combinations thereof. The casein may be provided in free form or in the form of a salt, for example, a sodium salt, a calcium salt or a potassium salt. Although the protein can comprise vegetable protein, in some embodiments the composition is gluten-free.

The protein may be extensively hydrolyzed protein hydrolysates prepared from acid or enzyme treated animal and vegetable proteins, such as casein hydrolysate, whey hydrolysate, casein/whey hydrolysate, soy hydrolysate, and mixtures thereof "Extensively hydrolyzed" protein hydrolysates means that the intact protein is hydrolyzed into peptide fragments in which a majority of the peptide fragments have a molecular weight less than 1,000 Daltons, preferably at least about 75% and most preferably at least about 95% of the peptide fragments having a molecular weight less than about 1,000 Daltons. Free amino acids and synthetic short peptide chains may be substituted for or added to the protein hydrolysates.

In an embodiment, the protein comprises whey protein micelles as described in U.S. Patent App. Pub. No. 2009/0035437 and its counterpart EP1839492A1 and as further characterized in C. Schmitt et al., Soft Matter 6:4876-4884 (2010) where they are referred to as whey protein microgels (WPM). Particularly, whey protein micelles are the micelles comprised in the whey protein micelles concentrate obtained by the process as disclosed in U.S. Patent App. Pub. No. 2009/0035437 and its counterpart EP1839492A1. Therein, the process for the production of whey protein micelles concentrate comprises the steps of: a) adjusting the pH of a whey protein aqueous solution to a value between 3.0 and 8.0; b) subjecting the aqueous solution to a temperature between 80 and 98° C.; and c) concentrating the dispersion obtained in step b). Thereby, the micelles produced have an extremely sharp size distribution, such that more than 80% of the micelles produced have a size smaller than 1 micron in diameter and preferably are between 100 nm and 900 nm in size. The whey protein micelles can be in liquid concentrate or in powder form. Importantly, the basic micelle structure of the whey proteins is conserved, whether in the liquid concentrate form, the powder form, or reconstituted from the powder, for example in water. The whey protein micelles are physically stable in dispersion, as a powder as well as during spray-drying or freeze-drying.

Non-limiting examples of suitable carbohydrates include starch, sucrose, lactose, glucose, fructose, corn syrup solids, maltodextrin, modified starch, amylose starch, tapioca starch, corn starch, xylitol, sorbitol or combinations thereof. Non-limiting examples of suitable lipids include vegetable fat (such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like), animal fats (such as milk fat), or combinations thereof. The source of fat may also be less refined versions of these fats (e.g., olive oil for polyphenol content).

The composition can be in any oral nutritional form, e.g. as a health drink, as a ready-made drink, optionally as a soft drink, including juices, milk-shake, yogurt drink, smoothie or soy-based drink; in a food bar; or dispersed in foods of any sort, such as baked products, cereal bars, dairy bars, snack-foods, soups, breakfast cereals, muesli, candies, tabs, cookies, biscuits, crackers (such as rice crackers), and dairy products.

The composition may be in the form of tablets, capsules, pastilles or a liquid, for example. The composition may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents.

Aspects of the subject matter described herein are set out in the following numbered clauses:

1. A method of treating or preventing impaired mobility in an older adult (for example an older adult being a low absorber or a non absorber of oleuropein, such as an individual having an intestinal microbiota lacking or low in bacteria having β-glycosidase activity and/or lacking or low in bacteria having esterase activity), the method comprising orally administering to the older adult an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase.

2. The method of Clause 1, wherein the older adult is an elderly individual.
3. The method of Clause 1, wherein the older adult has a condition selected from the group consisting of frailty, pre-frailty, sarcopenia, recovering from sarcopenia, osteoporosis, osteoarthritis, malnutrition, at risk of malnutrition, undergoing rehabilitation, scheduled to undergo rehabilitation within the next year, and combinations thereof.
4. The method of Clause 1 wherein the composition is administered daily for at least one month.
5. The method of Clause 1 wherein the at least one probiotic comprises a probiotic having β-glucosidase activity.
6. The method of Clause 1 wherein the at least one probiotic forms an oleuropein metabolite selected from the group consisting of oleuropein aglycone, hydroxytyrosol acetate, hydroxytyrosol, elenolic acid and mixtures thereof.
7. A method for stimulating bone formation and/or inhibiting bone resorption in an individual having a condition comprising an imbalance between bone formation and bone resorption, the method comprising orally administering to the individual (for example an individual being a low absorber or a non absorber of oleuropein, such as an individual having an intestinal microbiota lacking or low in bacteria having β-glycosidase activity and/or lacking or low in bacteria having esterase activity) an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase.
8. The method of Clause 7 wherein the condition is selected from the group consisting of osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof.
9. The method of Clause 7 wherein the composition is administered daily for at least one month.
10. The method of Clause 7 wherein the at least one probiotic having β-glycosidase activity is selected from the group consisting of a probiotic without esterase activity, a probiotic with esterase activity, and a mixture thereof.
11. A method of treating synovitis in an individual in need thereof, preventing synovitis in an individual at risk thereof, or treating or preventing articular cartilage degradation subsequent to synovitis in an individual having or recovering from synovitis, the method comprising orally administering to the individual (for example an individual being a low absorber or a non absorber of oleuropein, such as an individual having an intestinal microbiota lacking or low in bacteria having β-glycosidase activity and/or lacking or low in bacteria having esterase activity) an effective amount of a composition comprising oleuropein and at least one probiotic or enzyme selected from the group consisting of (i) a probiotic having β-glycosidase activity or a β-glycosidase, (ii) a probiotic having esterase activity or an esterase, (iii)

a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase.

12. The method of Clause 11 wherein the synovitis is associated with a condition selected from the group consisting of lupus, gout, rheumatoid arthritis, osteoarthritis, osteochondritis disease, osteoarthrosis and combinations thereof.

13. The method of Clause 11 wherein the composition is administered daily for at least one month.

14. The method of Clause 11 wherein the at least one probiotic comprises a probiotic having β-glucosidase activity.

15. A method of preventing or treating cartilage breakdown in an individual (for example an individual being a low absorber or a non absorber of oleuropein, such as an individual having an intestinal microbiota lacking or low in bacteria having β-glycosidase activity and/or lacking or low in bacteria having esterase activity), the method comprising orally administering to the individual an effective amount of a composition comprising oleuropein at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase.

16. The method of Clause 15 wherein the individual is an elderly individual.

17. The method of Clause 15 wherein the composition is administered daily for at least one month.

18. The method of Clause 15 wherein the at least one probiotic comprises a probiotic having β-glucosidase activity.

19. A composition comprising a combination of oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase, the composition comprises an amount of the combination that is effective to achieve an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof.

20. The composition of Clause 19 wherein the composition is a food product comprising a component selected from the group consisting of protein, carbohydrate, fat and combinations thereof.

21. A method of making a composition for achieving an effect selected from the group consisting of (i) maintaining or restoring bone or cartilage metabolism balance, (ii) maintaining or improving bone or cartilage health, (iii) maintaining or improving mobility in an older adult, (iv) treating or preventing synovitis, and (v) combinations thereof, the method comprising adding an effective amount of a combination of oleuropein and at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase to at least one ingredient selected from the group consisting of protein, carbohydrate, and fat.

22. The method of Clause 21, further comprising adding to the at least one ingredient a food additive selected from the group consisting of acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers, vitamins, minerals and combinations thereof.

23. A method of potentiating a therapeutic effect and/or a prophylactic effect of oleuropein in an individual (for example an individual being a low absorber or a non absorber of oleuropein, such as an individual having an intestinal microbiota lacking or low in bacteria having β-glycosidase activity and/or lacking or low in bacteria having esterase activity), the method comprising orally administering at least one probiotic or enzyme selected from the group consisting of (i) a probiotic having β-glycosidase activity or a β-glycosidase, (ii) a probiotic having esterase activity or an esterase, (iii) a probiotic having both β-glycosidase activity and esterase activity, (iv) a first probiotic having β-glycosidase activity and a second probiotic having esterase activity, (v) a probiotic having β-glycosidase activity and an esterase, (vi) a β-glycosidase and a probiotic having esterase activity and (vii) a β-glycosidase and an esterase to the individual.

24. The method of Clause 23, wherein the at least one probiotic is administered to the individual in the same composition as the oleuropein such that the at least one probiotic and the oleuropein are administered concurrently.

25. The method of Clause 23, wherein the at least one probiotic is administered to the individual in a composition separate from the oleuropein.

26. The method of Clause 23, wherein the at least one probiotic forms an oleuropein metabolite selected from the group consisting of oleuropein aglycone, hydroxytyrosol acetate, hydroxytyrosol, elenolic acid and mixtures thereof; and the oleuropein and the oleuropein metabolite provide the therapeutic effect and/or the prophylactic effect for a longer duration than would be obtained by administration of the oleuropein metabolite by itself.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating impaired mobility in an older adult being a low absorber or a non absorber of oleuropein, the method comprising orally administering to the older adult an effective amount of a composition comprising oleuropein and at least one probiotic selected from the group consisting of *Bifidobacterium longum* ATCC BAA-999, *Bifidobacterium longum* CNCM 1-2618, *Bifidobacterium animalis* CNCM 1-3446, *Streptococcus thermophilus* CNCM 1-3915, *Lactobacillus paracasei* CNCM 1-2116, *Lactobacillus rhamnosus* CGMCC 1.3724, *Lactobacillus johnsonii* CNCM 1-1225 and *Lactococcus lactis* CNCM 1-4154, and the composition does not contain rutin, wherein said low absorber or non absorber of oleuropein is a result of the older adult having an intestinal microbiota lacking or low in bacteria having β-glycosidase activity and/or lacking or low in bacteria having esterase activity.

2. The method of claim 1, wherein the older adult is an elderly individual.

3. The method of claim 1, wherein the older adult has a condition selected from the group consisting of frailty, pre-frailty, sarcopenia, recovering from sarcopenia, osteoporosis, osteoarthritis, malnutrition, at risk of malnutrition, undergoing rehabilitation, scheduled to undergo rehabilitation within the next year, and combinations thereof.

4. A method for stimulating bone formation and/or inhibiting bone resorption in an individual having a condition comprising an imbalance between bone formation and bone resorption, the method comprising orally administering to the individual an effective amount of a composition comprising oleuropein and at least one probiotic selected from the group consisting of *Bifidobacterium longum* ATCC BAA-999, *Bifidobacterium longum* CNCM 1-2618, *Bifidobacterium animalis* CNCM 1-3446, *Streptococcus thermophilus* CNCM 1-3915, *Lactobacillus paracasei* CNCM 1-2116, *Lactobacillus rhamnosus* CGMCC 1.3724, *Lactobacillus johnsonii* CNCM 1-1225 and *Lactococcus lactis* CNCM 1-4154, and the composition does not contain rutin, and the individual is a low absorber or a non absorber of oleuropein, wherein said low absorber or non absorber of oleuropein is a result of the individual having an intestinal microbiota lacking or low in bacteria having β-glycosidase activity and/or lacking or low in bacteria having esterase activity.

5. The method of claim 4, wherein the condition is selected from the group consisting of osteoporosis, Paget's disease, osteolysis adjacent a prosthesis, a metastatic bone disease, hyperthyroidism, hypercalcemia due to a cancer, multiple myelomas, a periodontal disease, osteoarthritis, osteopenia, a bone deficit resulting from a fracture, fracture healing, and combinations thereof.

6. A method of treating synovitis in an individual in need thereof, treating articular cartilage degradation subsequent to synovitis in an individual having r recovering from synovitis, the method comprising orally administering to the individual an effective amount of a composition comprising oleuropein and at least one probiotic selected from the group consisting of *Bifidobacterium longum* ATCC BAA-999, *Bifidobacterium longum* CNCM 1-2618, *Bifidobacterium animalis* CNCM 1-3446, *Streptococcus thermophilus* CNCM 1-3915, *Lactobacillus paracasei* CNCM 1-2116, *Lactobacillus rhamnosus* CGMCC 1.3724, *Lactobacillus johnsonii* CNCM 1-1225 and *Lactococcus lactis* CNCM 1-4154, and the composition does not contain rutin, and the individual is a low absorber or a non absorber of oleuropein, wherein said low absorber or non absorber of oleuropein is a result of the individual having an intestinal microbiota lacking or low in bacteria having β-glycosidase activity and/or lacking or low in bacteria having esterase activity.

7. The method of claim 6 wherein the synovitis is associated with a condition selected from the group consisting of lupus, gout, rheumatoid arthritis, osteoarthritis, osteochondritis disease, osteoarthrosis and combinations thereof.

8. The method of claim 1, wherein the composition is administered in the effective amount to enhance absorption of the oleuropein.

9. The method of claim 4, wherein the composition is administered in the effective amount to enhance absorption of the oleuropein.

10. The method of claim 6, wherein the composition is administered in the effective amount to enhance absorption of the oleuropein.

\* \* \* \* \*